United States Patent [19]

Aagesen

[11] Patent Number: 5,002,485
[45] Date of Patent: Mar. 26, 1991

[54] ORTHOPEDIC APPLIANCE

[76] Inventor: Larry K. Aagesen, 1056 Walnut Grove, Rochester Hills, Mich. 48064

[21] Appl. No.: 416,131

[22] Filed: Oct. 2, 1989

[51] Int. Cl.⁵ .............................................. A61C 3/00
[52] U.S. Cl. .......................................... 433/7; 433/18
[58] Field of Search .................................. 433/6, 7, 18

[56] References Cited

U.S. PATENT DOCUMENTS

| | | | |
|---|---|---|---|
| 3,977,082 | 8/1976 | Siatkowski | 32/14 E |
| 4,348,179 | 9/1982 | Nardella | 433/7 |
| 4,431,411 | 2/1984 | Witzig et al. | 433/6 |
| 4,433,956 | 2/1984 | Witzig | 433/7 |
| 4,468,196 | 8/1984 | Keller | 433/24 |
| 4,482,318 | 11/1984 | Forster | 433/7 |
| 4,573,914 | 3/1986 | Nord | 433/7 |

FOREIGN PATENT DOCUMENTS 590354  4/1959  Italy ......................................... 433/7

Primary Examiner—Cary E. Stone
Attorney, Agent, or Firm—Krass & Young

[57] ABSTRACT

An orthopedic appliance for correcting Class II malocclusions comprises a frontal portion configured to engage the mandibular and maxillary frontal arches and first and second side portions, posterior to the frontal portion, each configured to engage at least some of the maxillary molars. A universal screw assembly interconnects the frontal portions and the first and second side portions and operate to independently adjust the lateral spacing of the side portions from one another and the anterior-posterior spacing of the frontal portion from the side portions. The appliance is expanded in stages to maximize the utilization of corrective lower jaw movements which result from securing the appliance in the patient's upper mouth.

10 Claims, 2 Drawing Sheets

ORTHOPEDIC APPLIANCE

BACKGROUND OF THE INVENTION

The present invention relates generally to dental orthopedic correction and, more particularly, to an adjustable, functional and removable orthopedic appliance for correcting dental Class II malocclusions.

DESCRIPTION OF THE RELATED ART

A Class II malocclusion is defined as the malposition of the maxillary and mandibular teeth so that the lower dental arch is posterior to the upper dental arch resulting in loss of efficiency during movements of the jaw that are essential for mastication. In a Class II, division 1 malocclusion, the upper incisors are protruding and the occlusion is usually evidenced by an excessive overbite of the lower incisors. In a Class II, division 2 malocclusion the upper incisors are tipped lingually and the laterals are flared labially.

Class II malocclusions may be corrected utilizing either fixed appliances or functional, removable appliances, or a combination of both. Fixed appliances such as braces, are typically worn an average of 24 to 30 months to correct a Class II malocclusion. Fixed appliances also require either extra-oral force, intramaxillary elastics, or a combination of both to effect a basal maxilla-mandibular change and to eliminate the excessive overbite, overjet or apical base discrepancy.

Removable functional appliances may often eliminate the need for extra-oral force or intramaxillary elastics required by fixed appliances. A removable and functional orthopedic appliance corrects a Class II malocclusion by causing the entire mandible, or lower jaw, to move forward, freeing the condyle in the temporal mandibular joint from any possible growth restrictions from the dominant retrusive muscular activity associated with the inherent Class II malocclusion. The forward movement of the mandible is caused by a stretch reflex initiated by introducing the orthopedic appliance into the patient's mouth, causing the muscles to pull the mandible in an anterior direction.

Present orthodontic practice utilizes a series of two or more removable functional orthopedic appliances to correct a Class II type of malocclusion. Examples of these devices are commonly known in the orthodontic profession as "Saggital," "Frankel," "Bionater," and "Ortho Redir Corrector" devices. Each successive appliance is elongated along an anterior-posterior medial line relative to the previously used appliance and as the treatment progresses and the mandible more closely aligns with the maxilla, the second or third appliances of the series is used by the patient. With each successive appliance the mandible is repositioned more closely to a correctly aligned state relative to the maxilla while concurrently restricting maxillary forward growth.

Adjustable, functional and removable devices have also been proposed which eliminate the need for using two or more of the above-described orthopedic appliances. For example, U.S. Pat. No. 4,433,956 discloses an adjustable, functional and removable orthopedic corrector having an anterior segment and a posterior segment interconnected by two expansion screw assemblies. As treatment of the Class II malocclusion progresses, each of the two expansion screw assemblies are turned, separating the anterior and posterior segments of the corrector with resultant forward movement of the mandible It is necessary, however, to carefully adjust each expansion screw assembly equally to result in the proper correction of the malocclusion.

U.S. Pat. Nos. 4,348,179; 3,977,082 and 4,468,196 disclose various other adjustable orthodontic appliances fitting into the palatal cavity of the mouth for treatment of various orthodontic dysfunctions. However, none of these patents proposes a device for the treatment and correction of Class II malocclusions.

There is a need for a single orthopedic appliance for correcting Class II malocclusions which eliminates the need for sequentially employing two or more devices. The appliance should be easy to fabricate, comfortable for the user to wear, easily adjustable and effective in the correction of the Class II malocclusions in as short as time possible. The present invention addresses these problems by providing a single, removable, functional, active appliance for use in the full course of treatment and correction of Class II malocclusions. In addition, the appliance of the present invention is relatively comfortable to wear, thereby eliciting a high degree of patient compliance. These and other advantages of the present invention will be apparent from the drawings, discussion, description and claims which follow.

SUMMARY OF THE INVENTION

The present invention provides an orthopedic appliance for correcting Class II malocclusions comprising a frontal portion configured to engage the mandibular and maxillary frontal arches of the mouth. The frontal portion includes a cavity corresponding to at least a portion of the inner and outer surfaces of the mandibular incisors and which engages the rear surface of the maxillary incisors. Engagement of the mandibular incisors into the cavity over an extended period of time corrects the Class II malocclusion. The frontal portion further includes a pair of ball clasps which engage the front surfaces of the maxillary incisors.

The appliance further includes first and second side portions, each configured to engage at least some of the maxillary molars. Each side member includes a retaining clasp for engaging the maxillary molars and securing the device into the palatal cavity of the mouth. The side portions may also include other orthodontic attachments such as distalizing springs and the like to perform other orthodontic corrections.

The orthopedic appliance of the present invention further includes adjustment means interconnecting the frontal portion to the first and second side portions. The adjustment means includes a first expansion screw interconnecting the side members and operative to adjust the lateral spacing therebetween and a second expansion screw associated with the frontal member to adjust the anteriorposterior spacing between the frontal portion and the two side portions. In this manner, the present invention provides a single appliance for correcting Class II malocclusions which is easily adjustable in two directions.

DETAILED DESCRIPTION OF THE PREFERRED EMBODIMENT

Figure 1:
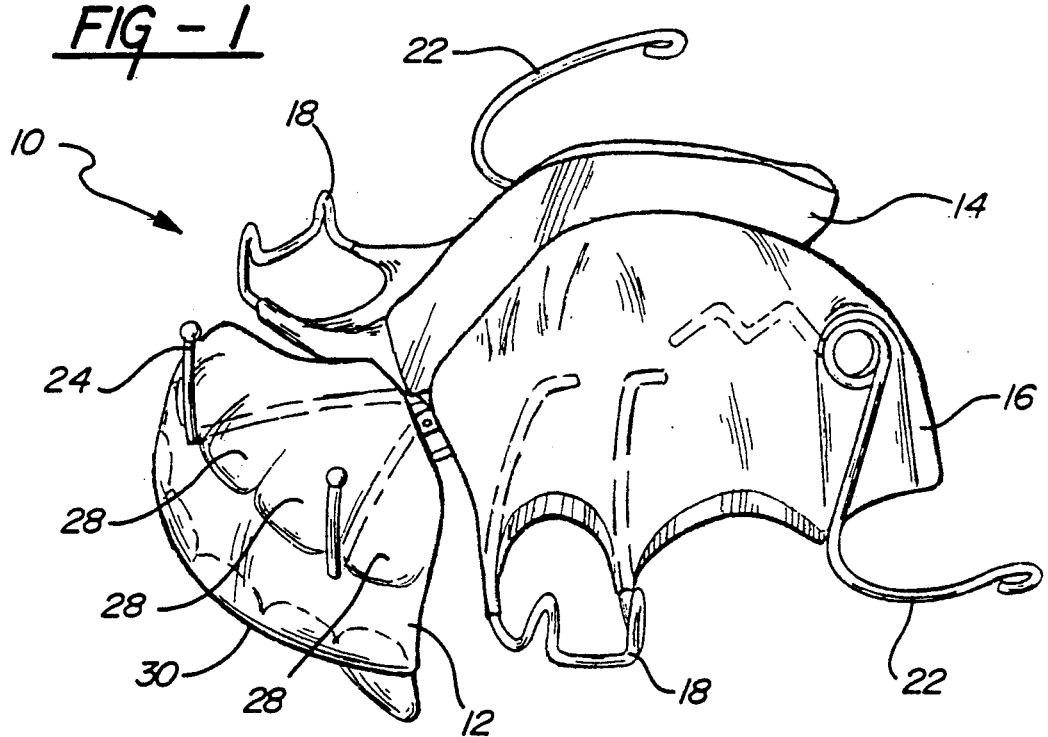
FIG. 1 is a perspective view of an orthopedic appliance of the present invention.

Referring now to the drawings, as is shown in FIG. 1, an orthopedic appliance 10 comprises a frontal portion 12, a first side portion 14 and a second side portion 16, molded to conform to the interior of the patient's mouth. Orthopedic appliance 10 is removably secured in the palatal cavity of a patient's mouth by retentive springs and clasps as will be explained below. The frontal portion 12 is configured to engage at least a portion of the mandibular and maxillary frontal arches when the mouth is closed, while the first and second side portions 14, 16 engage the interior sides of at least some of the maxillary molars.

Frontal portion 12, first side portion 14 and second side portion 16 are fabricated from a synthetic polymeric material, preferably a tissue compatible acrylic, using established techniques known in the dental art. In one such technique, a plaster cast from an alginate mold is made of the patient's mouth and dentition in the construction bite position. The construction bite is defined as the amount of forward movement of the mandible and opening of the mandible which the patient self-induces at the doctor's direction prior to treatment. Orthopedic appliance 10 is molded using the shape taken from the plaster cast. Retaining clasps 18, ball clasps 24 and various other orthopedic attachments, such as distalizing springs 22, are placed in the mold at the desired locations and are embedded into place in the acrylic during the molding process.

Figure 2:
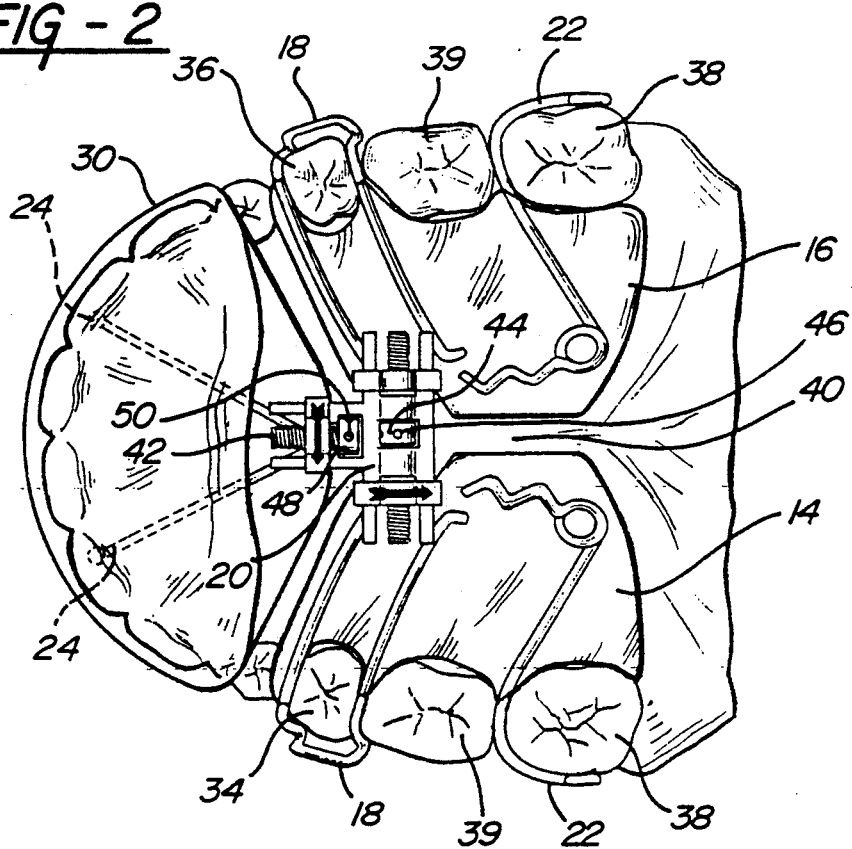
FIG. 2 is a bottom plan view of the orthopedic appliance of FIG. 1 seated in the palatal cavity of a user.
Figure 3:
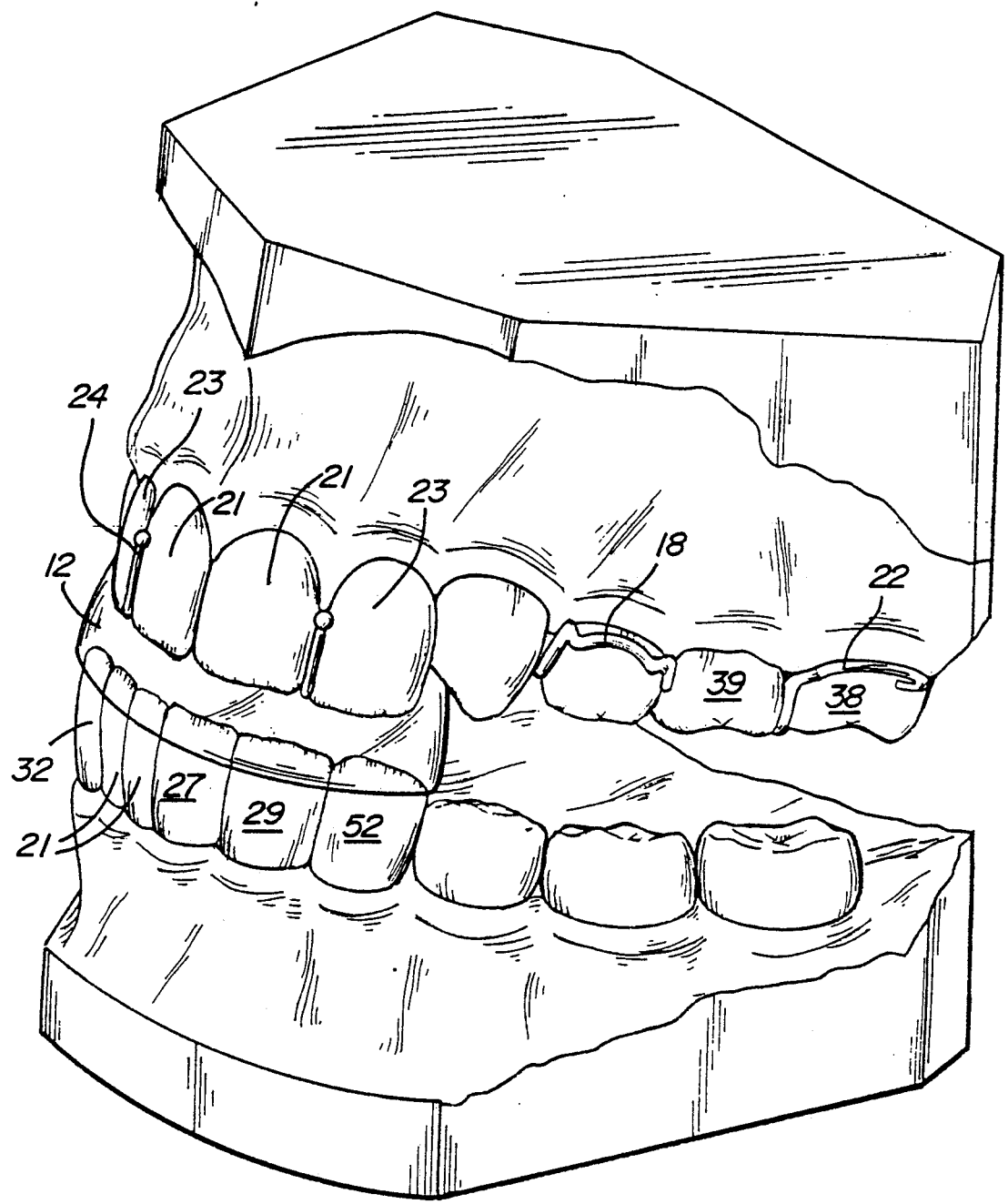
FIG. 3 is a perspective view of the orthopedic appliance of the present invention fitted into a plaster model of a mouth with closed jaws.

FIGS. 2 and 3 show the orthopedic appliance 10 in place in a plaster model of in the mouth of a 7-year old patient. This patient has not completely lost all of her deciduous or "baby" teeth as will be noted by those skilled in the art. This model is shown as an example only and in no way is meant as a limitation upon the present invention. Although the appliance 10 may be used to correct Class II malocclusions at any stage during a patient's life, the appliance 10 is most favorably used while the patient is actively growing, i.e., at or before puberty.

As is particularly illustrated in FIG. 3, the ball clasps 24 are embedded in the frontal portion 12 and act to engage the front surface of the maxillary arch between the central 21 and lateral 23 maxillary incisors. The top of the frontal portion 12 further includes indentations 28 (best seen in FIG. 1) for engaging the rear surfaces of the maxillary incisors 21,23. The bottom of frontal portion 12 includes a cavity 30, as shown in phantom in FIG. 1 and shown more clearly in FIGS. 2 and 3, for receiving at least a portion of the inner and outer surfaces of the central 27 and lateral 29 mandibular incisors as well as the mandibular cuspids 32 therein.

The first side portion 14 and the second side portion 16 are molded to conform to the roof of the patient's upper mouth. As shown more clearly in FIG. 2, the first and second side portions 14,16 respectively, include retaining clasps 18, (in this case known as Adams clasps), for engagement with molars 34,36. Retaining clasps 18 and ball clasps 24 cooperate to actively secure orthopedic appliance 10 firmly in the roof of the patient's mouth. This particular feature represents an improvement over prior art devices which utilize tongue position and intimate fit on the upper teeth to hold the appliance in position.

In the illustrated embodiment, the first side portion 14 and the second side portion 16 further include molar distalizing springs 22 which are integral in action with the lower jaw advancement bite. As shown in FIGS. 2 and 3, molar distalization springs 22 engage the first permanent (6 year) molars 38 along their exterior surfaces and between the first permanent molars and the adjacent (deciduous or permanent) second 39 molars. Distalizing springs 22 force the first permanent molars to move distally during the treatment of the Class II malocclusions. Various other orthodontic attachments and/or springs for causing buccal, labial, rotational and/or lingual movement of individual teeth may also be molded into appliance 10. Orthopedic appliance 10 further includes adjustment means such as universal screw assembly 20, for altering the spatial relationship between the front 12 and side 14,16 portions. The universal screw assembly 20 may preferably be fabricated from stainless steel, chromium-nickel alloys, non-ferrous metals, or combinations thereof. The universal screw assembly 20 includes a first expansion screw 40 which interconnects the first side portion 14 to the second side portion 16 and operates to adjust the lateral spacing therebetween. The first expansion screw 40 includes an adjuster member 44 containing a plurality of holes 46 for receiving the end of an adjustment tool, such as a small allen wrench key therein. Holes 46 are equidistantly, circumferentially spaced on adjuster member 44 and the pitch of the screw is such that a 90 degree rotation of adjuster member 44 translates into a lateral spacing increase of approximately one-quarter millimeter between the first side portion 14 and the second side portion 16. By utilizing a single adjustment mechanism or expansion screw 40 in this manner, expansion of the device can be easily and accurately adjusted without the need for adjusting two separate screw assemblies as is required in prior art devices.

Adjusting the first expansion screw 40 to cause the lateral spacing between the first and second side portions to increase and to increase maxillary arch width. This is a necessary step because, as the upper molars move distally as a result of a molar distalizing springs 22, the maxillary arch width must increase as growth occurs in order to reduce cross bite occurrence.

The universal screw assembly 20 includes a second expansion screw 42 which is similar to the first expansion screw 40 in that it also includes an adjuster member 48 having a plurality of adjustment holes 50. As described above with reference to the first expansion screw 40, holes 50 are equally spaced around adjuster member 48 so that the second expansion screw 42 can be adjusted by inserting the tool into the hole and moving it relative to a threaded shaft assembly. As before, a 90 degree rotation of adjuster 48 causes the frontal portion 12 to moVe either posteriorly or anteriorly to the first 14 and second side portions 16, a distance of about one-quarter millimeter.

As the second expansion screw 42 is turned in the direction of the arrow, the anterior and posterior segments of the appliance are separated, resulting in forward movement of the mandible. Also, an increase in distance between the frontal portion 12 and the posterior portion 14,16 causes an increase in the upper anterior tooth protrusive guidance as well as movement of the maxillary posterior teeth distally. This upper activation also causes an equal and opposite distalizing effect on the maxillary posterior teeth.

Appliance 10 differs from prior art orthopedic appliances in that it moves the upper first permanent molars substantially to the posterior because of the neurologically stimulated anchorage which produces a distalizing, posterior force component in the maxilla equal to the forward stretching, growth stimulating force of the mandibular arch and temporal mandibular joint. The appliance 10 also allows lower posterior alveolar development while holding the lower anterior teeth in position which reduces the usual deep overbite. Mandibular growth and maxillary retraction decrease the amount of original overjet. The construction of the appliance also allows vertical alveolar growth in the posterior parts of the mouth to occur faster and in greater differential to the anterior teeth which are fitted and stabilized in the appliance. This decreases the amount of original overbite.

DESCRIPTION OF OPERATION OF THE PREFERRED EMBODIMENT

After the orthopedic appliance 10 has been molded to fit the patient's mouth, it is secured against the roof of the patient's mouth by the action of Adams clasps 18 and ball clasps 24 on the teeth and the intimate fit of the appliance. Initially, the orthopedic appliance is adjusted to be retentive only with the mandible forward and the bite open. It should be noted that each patient's treatment is individualized, with some patients being required to wear the device for longer periods of time than other patients. An average treatment period lasts between 6-18 months depending on several factors, including the severity of the malocclusion, the age of the patient, the patient's response to treatment and the patient's cooperation in the counsel treatment. Even in the initially adjusted position, orthopedic appliance 10 is molded so that when the mandible is in a closed position it will be forced forward of its pre-treatment position relative to the maxillary arch.

After approximately one month, the molar distalizing springs 22 and expansion screws 40, 42 are activated. Typically, at one month intervals, the patient removes the orthopedic appliance 10, and using a small tool such as the allen wrench or key as described above, turns each expansion screw 40,42 within assembly 20 to effect a posterior-anterior expansion of approximately ¼ millimeter. Lateral expansion of appliance 10 with screw 40 is performed as needed and directed by the patient's orthodontist. Each successive month for a total of 6–18 months depending upon the patient's response to treatment, the patient turns each expansion screw 40,42 approximately ¼ millimeter per month, resulting in an aggregate of approximately 1½–4½ millimeters of expansion between frontal portion 12 and first and second side portions 14,16. Occasionally, use of the appliance 10 is discontinued for a short period of time, typically 3–6 months, so that the orthodontist can evaluate growth changes in the mandible and maxilla prior to using fixed appliances. The appliance 10 may be used in conjunction with fixed appliances where the malocclusion is especially difficult to treat or where other positional irregularities exist. The gradual expansion of appliance 10 avoids patient discomfort and possible periodontal necrosis and root resorption which might result from an immediate expansion to the maximum extent allowed by expansion screw assemblies 20. When full expansion is reached, the lower jaw or mandible has moved with respect to the upper jaw to a position beyond the construction bite, through a series of successively more forward positions relative to the maxilla. The orthopedic appliance 10 must usually be worn by the patient for approximately 6–18 months to achieve the result of a Class I occlusion. During this period, the upper teeth are moving posteriorly relative to the mandible and the mandible is moving forward.

The present invention is designed to correct Class II malocclusions by changes in the muscular and structural growth of the temporal mandibular joint. For instance, during the initial three-month period after insertion of the orthopedic appliance, there is a rapid change about the mandibular condyle and muscle function. Due to the position of the frontal portion 12 of appliance 10 beyond the previously established position of the mandible, the skeletal and muscular growth changes can result in permanent movement anteriorly of the mandible relative to the maxilla. This anterior movement of the mandible even occurs with the expansion screw assemblies closed.

After the treatment period is completed and appliance 10 is no longer used, the mandible generally moves posteriorly about one millimeter which generally results in full correction of the mandibular-maxilla relationship.

The patient is instructed to wear the orthopedic appliance at all times during the treatment period except when eating, engaging in active sports and brushing the teeth. The appliance 10 is designed so that at all times of engagement the appliance is active, even when the patient moves his or her jaws, swallows or talks. The activation of the appliance 10 exerts a gentle pressure on the teeth and dental arches. This orthopedic appliance 10 is designed to fit intimately in the mouth and be capable of easy and frequent removal and replacement by the patient, much like a dental plate. This precise fit of the lower incisors forward into the appliance makes the patient to close his jaws together in the new relationship. This is a distinct advantage over the prior art.

In light of the foregoing, it should be apparent that many variations are possible within the scope of the present invention. For example, the orthopedic appliance may be configured to include various orthodontic attachments such as labial wires and individual tooth moving springs so that the orthopedic appliance of the present invention performs orthodontic corrections at the same time as the Class II malocclusion is treated. The appliance may be adapted for use in Class II, division 2 as well as Class I malocclusions. Also, the treatment period will be generally be the same for every patient although many variations are necessary for each individual patient. Accordingly, the foregoing drawings, discussion and description are merely meant to be illustrative of particular embodiments of the invention and not limitations upon the practice thereof. It is the following claims including all equivalents which define the scope of the invention.

I claim:

1. An orthopedic appliance for treating Class II malocclusions comprising:
    a frontal portion configured to engage the mandibular and maxillary frontal arches;
    first and second side portions, each configured to engage at least some of the maxillary molars; and
    a universal screw, which comprises a base member having a first and a second expansion screw associated therewith, interconnecting said frontal portion and said first and second side portions, said first screw operative to independently adjust the lateral spacing of the side portions from one another and said second screw operative to adjust the anteriorposterior spacing of the frontal portion from the side portions.

2. An orthopedic appliance as in claim 1, wherein said frontal portion includes a cavity configured to correspond to at least a portion of the inner and outer surfaces of the mandibular incisors and/or cuspids.

3. An orthopedic appliance as in claim 1, wherein said frontal portion is configured to engage the rear surface of the maxillary incisors and further includes a pair of ball clasps configured to engage the front and interproximal surface of the maxillary incisors.

4. An orthopedic appliance as in claim 1, wherein said side portions each include a retaining clasp configured to engage a maxillary deciduous molar or bicuspid tooth.

5. An orthopedic appliance as in claim 1, wherein at least one of said side portions includes a spring operative to effect molar distalizing.

6. An orthopedic appliance as in claim 1, wherein said universal screw is fabricated from a material selected from the group consisting essentially of stainless steel, chromium-nickel alloys, non-ferrous metals, and combinations thereof.

7. An orthopedic appliance as in claim 1, wherein said frontal portion and said side portions are fabricated from synthetic polymeric materials.

8. An orthopedic appliance as in claim 7, wherein said synthetic polymeric material is an acrylic material.

9. An orthopedic appliance for treating Class II malocclusions comprising:

a frontal portion configured to engage the mandibular and maxillary frontal arches, said frontal portion including a cavity configured to correspond to at least a portion of the inner and outer surfaces of at least some of the mandibular teeth and a pair of ball clasps configured to engage the front surface of the maxillary incisors;

first and second side portions, each configured to engage at least some of the maxillary molars, each of said side members including a retaining clasp configured to engage a maxillary molar; and adjustment means interconnecting said frontal portion and said first and second side portions, said adjustment means including a first expansion screw interconnecting said side portions and operative to adjust the lateral spacing thereof and a second expansion screw associated with the frontal portion and operative to adjust the anterior-posterior spacing between said frontal portion and said side portions.

10. An orthopedic appliance for treating Class II malocclusions comprising:

a frontal portion configured to engage the mandibular and maxillary frontal arches;

first and second side portions, each configured to engage at least some of the maxillary molars; and unitary adjustment means interconnecting said frontal portion and said first and second side portions and operative to independently adjust the lateral spacing of the side portions from one another and the anterior-posterior spacing of the frontal portion from the side portions.

* * * * *